United States Patent [19]
Al-Razzak et al.

[11] Patent Number: 6,008,192
[45] Date of Patent: Dec. 28, 1999

[54] HYDROPHILIC BINARY SYSTEMS FOR THE ADMINISTRATION OF LIPOPHILIC COMPOUNDS

[75] Inventors: Laman A. Al-Razzak, Highland Park; Panayiotis Pericleous Constantinides; Dilip Kaul, both of Gurnee, all of Ill.; John M. Lipari, Racine, Wis.; Lisa L. McChesney-Harris; Bashar Y. Abdullah, both of Veron Hill, Ill.

[73] Assignee: Abbott Laboratories, Abbott Park, Ill.

[21] Appl. No.: 09/041,881

[22] Filed: Mar. 12, 1998

Related U.S. Application Data

[63] Continuation-in-part of application No. 08/816,375, Mar. 12, 1997, abandoned.

[51] Int. Cl.$^6$ .............................. A61K 9/10; A61K 9/50; A61K 47/34
[52] U.S. Cl. .............................. 514/11; 514/885; 514/975
[58] Field of Search ................................ 514/11, 885, 975

[56] References Cited

U.S. PATENT DOCUMENTS

| | | | |
|---|---|---|---|
| 4,117,118 | 9/1978 | Harri et al. | 514/11 |
| 4,388,307 | 6/1983 | Cavanak | 514/11 |
| 5,342,625 | 8/1994 | Hauer et al. | 514/11 |
| 5,614,491 | 3/1997 | Walch et al. | 514/11 |
| 5,766,629 | 1/1998 | Cho et al. | 424/455 |

FOREIGN PATENT DOCUMENTS

| | | |
|---|---|---|
| 2642650 | 10/1990 | France . |
| WO 92/09299 | 6/1992 | WIPO . |
| WO 94/23733 | 10/1994 | WIPO . |
| 9425068 | 11/1994 | WIPO . |

OTHER PUBLICATIONS

Derwent Abstract 89–088668, "Drugs of Soluble Cyolosporin Powder" Feb, 1989.

S.A. Charman et al., "Self–Emusifying Drug Delivery Systems: Formulation and Biopharmaceutic Evaluation of an Investigational Lipophilic Compound," *Pharmaceutical Research*, 9 (1): 87–93 (1992).

N.H. Shah et al., "Self–Emusifying Drug Delivery Systems (SEEDS) With Polyglycolyzed Glycerides For Improving In Vitro Dissolution and Oral Absorption of Lipophilic Drugs," *International Journal Of Pharmaceutics*, 106: 15–23 (1994).

*Primary Examiner*—Frederick Krass
*Attorney, Agent, or Firm*—Andreas M. Danckers

[57] ABSTRACT

Binary pharmaceutical compositions comprising (i) a cyclosporine compound, (ii) a hydrophilic phase and (iii) a surfactant provide bioavailability of the active ingredient which is equivalent to that provided by ternary compositions, but without the need for a lipophilic phase.

12 Claims, No Drawings

HYDROPHILIC BINARY SYSTEMS FOR THE ADMINISTRATION OF LIPOPHILIC COMPOUNDS

This application is a continuation-in-part of U.S. patent application Ser. No. 08/816,375, filed Mar. 12, 1997, now abandoned.

TECHNICAL FIELD

The present invention relates to pharmaceutical compositions containing lipophilic medicinal compounds, suitable for oral as well as topical, local and other routes of administration. In particular, the invention relates to binary formulations of cyclosporines which comprise a hydrophilic phase and one or more surfactants, but which lack a lipophilic phase.

BACKGROUND OF THE INVENTION

Pharmaceutical compounds which are highly lipophilic present considerable formulation challenges. Because of their low solubility in aqueous media, including the contents of the mammalian digestive tract, they often suffer from poor or variable bioavailability when given orally or via other routes that require transmembrane absorption. Examples of such medicinal compounds include the immunosuppressants cyclosporine and FK506 (tacrolimus); protease inhibitors such as ritonavir; central nervous system drugs such as tiagabine; and anti-inflammatory agents such as zileuton and other 5-lipoxygenase inhibitors.

One method of formulating lipophilic compounds is to combine them with glyceride carriers which form emulsions upon mixing with water. Emulsions are described, for example, in U.S. Pat. No. 4,388,307 issued to Cavanak, a commercial example of which is the cyclosporine-containing product SANDIMMUNE® oral solution. This product comprises the emulsifier LABRAFIL® (a polyoxyethylated kernel oil), olive oil and alcohol, with the compound cyclosporin A present at a concentration of 100 mg/ml. Cavanak suggests that such glyceride carriers may assist in alleviating problems of physical instability such as precipitation of the drug from solution, and may also enable higher plasma concentrations.

More recently, it has been proposed that a preferred vehicle for lipophilic compounds is the so-called "self-emulsifying drug delivery system" which, when exposed to an aqueous medium, forms a fine oil-in-water emulsion with little or no agitation. The property of self-emulsification permits such formulations to be administered in concentrated form, as for example in a hard gelatin or soft elastic capsule, with the expectation that a fine emulsion will be formed in the digestive tract. Moreover, it has been suggested that self-emulsifying formulations, when given orally, may offer improvements in both the rate and extent of absorption of the medicinal compound and can result in reduced variability in plasma concentration profiles. (See, S. A. Charman el al., *Pharmaceutical Research* 9(1):87–93 (1992), and N. H. Shah et al., *International Journal of Pharmaceutics* 106:15–23 (1994).) Additionally, emulsions which have been prepared by combining a self-emulsifying pre-concentrate with an aqueous medium appear to benefit, due to their small droplet diameter, from improved physical stability when compared with conventional emulsions.

Previously-disclosed self-emulsifying systems include those in which a lipophilic drug is combined with mixtures of (i) medium-chain triglycerides and nonionic surfactants, (ii) vegetable oils and partial glycerides such as polyglycolyzed glycerides or medium-chain mono- and diglycerides, or (iii) vegetable oils and nonionic surfactants such as polysorbate 80 or PEG-25 glyceryl trioleate. Other formulations have been characterized as self-emulsifying, including the above-mentioned SANDIMMUNE® cyclosporine formulation; however, these additionally contain a substantial amount of a solubilizing agent or solvent such as ethanol, rendering them unsuitable for certain uses such as filling into gelatin capsules, from which the solvent can readily escape.

Self-emulsifying formulations which seek to overcome this drawback are disclosed by Hauer et al in U.S. Pat. No. 5,342,625. In these formulations, a "microemulsion pre-concentrate" of a cyclosporine is formed by combining the drug with (I) a hydrophilic phase, (II) a lipophilic phase, and (III) a surfactant, as well as optional thickeners, antioxidants or other excipients. Unfortunately, the complexity of these ternary formulations may make them costly and difficult to manufacture.

There exists, consequently, a need for formulations of lipophilic drugs such as cyclosporines that are simpler and easier to prepare than the ternary systems described above. Orban et al., in PCT Publication No. WO 92/09299, propose homogenized cyclosporine-containing formulations that comprise propylene glycol, ethanol and a polyoxyethylene/polyoxypropylene block copolymer, while Fleck et al., in PCT Publication No. WO 94/23733, disclose cyclosporine formulations containing CREMOPHOR and/or TRANSCUTOL. However, additional formulations are sought which offer an advantageous combination of physical stability, desirable pharmacokinetics and/or ease of manufacture.

SUMMARY OF THE INVENTION

Surprisingly, it has now been found that many of the problems associated with the administration of lipophilic compounds such as cyclosporines may be overcome by the use of a simple binary system of excipients comprising (i) a hydrophilic phase and (ii) a surfactant or mixture of surfactants. In particular, the invention provides pharmaceutical compositions containing a cyclosporine compound in combination with a hydrophilic solvent phase and one or more surfactants, but not containing lipophilic solvents. Such binary formulations are novel where the hydrophilic phase is other than a $C_1$-to-$C_5$-alkyl or tetrahydrofurfuryl di- or partial ether of a low molecular weight mono- or polyoxyalkanediol, and the surfactant is other than an ethylene oxide/propylene oxide block copolymer. Moreover, the cyclosporine-containing formulations of the present invention are stable, simple to prepare, and commercially attractive by virtue of their pharmacokinetic properties.

As used herein, the terms "binary system", "binary composition" and "binary system of excipients" denote those formulations and compositions which contain, in addition to the active ingredient or ingredients, a combination of at least one hydrophilic solvent and at least one surfactant, but which lack a lipophilic solvent. Such compositions may be supplemented with additional adjuvants and still be considered "binary", so long as they do not include a lipophilic solvent phase.

To prepare the pharmaceutical compositions of the invention, a binary system of the invention is combined with a lipophilic active ingredient, such as a cyclosporine compound. The term "cyclosporine" as used herein refers to one or more of the cyclosporines, and especially to cyclosporin A, as described in U.S. Pat. No. 4,117,118 issued to Härri et al. and incorporated herein by reference.

If desired, binary compositions of the present invention may be selected which are bioequivalent to compositions that use the ternary excipient systems of the prior art; that is, when such binary and ternary compositions containing equal amounts of active ingredient are administered separately to comparable test subjects, about the same amount of active ingredient will be delivered to the subjects' bloodstreams by the inventive composition as by the ternary composition. The amount of drug delivered (or other pharmacokinetic property) may be measured by any of the methods known in the art, as for example the maximum plasma concentration ($C_{max}$), the time from dosing until the maximum plasma concentration is reached ($T_{max}$), and the integral or time-course of plasma concentration over time (area under the curve, or AUC).

As described earlier, the binary systems of the invention comprise a hydrophilic phase and one or more surfactants. Unless otherwise specified, the term "hydrophilic component" refers to water or to a pharmaceutically acceptable hydrophilic solvent, compound, carrier, excipient or diluent. The term "hydrophilic phase" refers to that portion of the composition that is hydrophilic, which phase can be a single component or a mixture of components.

The term "surfactant" as used herein describes that portion of a composition of the invention which comprises one or more surfactants. The surfactants may be any of the known pharmaceutically acceptable surfactants, including nonionic, anionic and cationic surfactants. A single surfactant or a mixture of surfactants may be used.

Unless otherwise specified, all percentages are weight percentages based on the total weight of the pharmaceutical composition.

DETAILED DESCRIPTION OF THE INVENTION

In binary compositions according to the present invention, the hydrophilic phase may comprise one or more of the known pharmaceutically acceptable hydrophilic solvents or excipients that are capable of solubilizing cyclosporine, with the exception of $C_1$-to-$C_5$-alkyl or tetrahydrofurfuryl di- or partial ethers of low molecular weight mono- or poly-oxy alkanediols. Suitable classes of hydrophilic compounds include, for example, pharmaceutically acceptable alcohols including the polyethylene glycols.

Particular hydrophilic phase components useful in the compositions of the invention include, but are not limited to, water; ethanol; benzyl alcohol; propylene glycol; low molecular weight polyethylene glycols having a molecular weight of up to about 1,000; glycerol; and dimethyl isosorbide. Of these, anhydrous ethanol and especially propylene glycol are preferred hydrophilic phase components. However, it may be desirable in some circumstances to eliminate ethanol and other relatively volatile solvents from the formulation in order to avoid some of the drawbacks thereof, which include (i) incompatibility with certain capsule materials (such as soft gelatin) when filled into capsules for oral dosing, (ii) loss of solvent and formulation instability over time, (iii) solvent loss during manufacture, and (iv) possible patient intolerance of the solvent; in such cases, formulations of the invention which are free or substantially free from the more volatile solvents are especially preferred. Alternatively, fill-capsule incompatibilities may be avoided by preparing the compositions of the invention as semi-solids and placing them into hard gelatin rather than soft elastic capsules, thereby permitting the use of ethanol and similar solvents.

The hydrophilic phase, comprising one or more hydrophilic solvents, typically comprises about 10% to about 90% by weight of the pharmaceutical composition. The precise amount used will vary depending on the nature of the hydrophilic compound or compounds used, the amount and type of active ingredient present, the dosage form, and other factors known in the art. Preferably the hydrophilic phase comprises about 20% to about 80%, and more preferably about 30% to about 60%, by weight of the pharmaceutical composition of the invention. Where non-aqueous hydrophilic components are used, water can be included in the formulation at levels varying from about 0.5% to about 10%, or preferably from about 1% to about 5%, based on total weight of the composition.

The binary systems of the present invention also comprise at least one surfactant in combination with the above hydrophilic phase. While not intending to be bound by theory, the surfactant is believed to assist in the formation of a micellar system or a microsuspension upon contact with an aqueous medium such as gastrointestinal fluids in a way that the solubility of the active ingredient is enhanced; the size of the particles present in this micellar or microsuspension system are in the sub-micron (sub-micrometer) range and can vary over time. Any of the known pharmaceutically acceptable surfactants may be used, including nonionic, anionic, cationic, and combinations thereof, with the exception of ethylene oxide/propylene oxide block copolymers. Nonionic surfactants are preferred, and especially those surfactants having a hydrophile/lipophile balance (HLB) of 10 or more. Alternatively, certain combinations of high- and low-HLB surfactants may be utilized; preferably, such mixed surfactants are used in a ratio such that the aggregate surfactant HLB (when weighted according to proportions used) remains in excess of 10.

Examples of suitable surfactants include, but are not limited to, polyoxyethylene derivatives of natural or hydrogenated vegetable oils such as castor oil; polyoxyethylene-sorbitan fatty acid esters, such as mono-, di- and tri-lauryl, palmityl, stearyl and oleyl esters; alkyl/dialykyl sulfate, sulfonate or sulfosuccinate salts such as sodium lauryl sulfate and dioctyl sodium sulfosuccinate; polyoxyethylene fatty acid esters; phospholipids such as lecithins; trans-esterification products of natural vegetable oil triglycerides and polyalkylene polyols; sorbitan fatty acid esters; pentaerythritol fatty acid esters; polyoxyethylene glycol alkyl ethers and esters; and the like. The surfactants may be used alone or in combination.

Although any pharmaceutically acceptable surfactant may be used in the binary system of the invention, certain surfactants are preferred. These include polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of polyoxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decaglyceryl mono- and dioleate; and combinations of these. The polyoxyethylene castor oil derivatives CREMOPHOR® EL and CREMOPHOR® RH40 are particularly preferred.

In some instances (as when the compositions of the present invention are prepared as semi-solids, described below), it may be particularly advantageous to use at least one additional low-HLB surfactant along with one or more of the above high-HLB surfactants. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.). Of these, the sorbitan oleates, and especially SPANS 80, are preferred low-HLB auxiliary surfactants, and most particulary when used in combination with CREMOPHOR®.

The surfactant phase generally comprises about 10% to 90% by weight of the composition. Preferably the surfactant comprises about 20% to about 70% of the composition, and more preferably about 40% to about 60%, by weight.

The active ingredient, for example a cyclosporine, will normally be present in amounts ranging from about 0.03% to about 15% by weight of the composition. In a preferred embodiment, the active ingredient is present in an amount of about 5% to about 15% by weight, with about 10% to about 13% being particularly preferred. It is intended, however, that the choice of a particular level of active ingredient will be made in accordance with factors well known in the medicinal arts, including mode of administration and the size and condition of the subject.

If desired, the compositions of the invention may additionally comprise other pharmaceutically acceptable excipients, such as thickeners, fillers, diluents, flavoring agents, coloring agents, antioxidants, preservatives such as antibacterial or antifungal agents, and the like. Such additives, if present, may typically comprise about 0.01% to about 10% by weight of the composition. Suitable thickening agents include any of those known in the art, as for example pharmaceutically acceptable polymers and/or inorganic thickeners. Such agents include, but are not limited to, polyacrylate homo- and co- polymers; celluloses and cellulose derivatives; polyvinyl pyrrolidones; polyvinyl resins; and silicates; of these, polyvinylpyrrolidone is preferred.

When desired, the compositions of the present invention may be prepared as semi-solid rather than liquid formulations by addition a greater proportion of appropriate thickening or solidifying agents. Such preparations may be particularly useful as fills for hard gelatin (as opposed to soft gelatin) capsules. Without intending to be limited by theory, it is believed that, when used as described herein, these solidifying agents modify the physical properties of the composition but do not significantly function as solvents or solubilizers of the active ingredient.

Solidifiers suitable for the preparation of semi-solid compositions include, but are not limited to, polyethylene glycols having a molecular weight of more than about 1,000, such as PEG 1450 and PEG 3350; stearyl alcohol; and colloidal silicon dioxide (CAB-O-SIL® M-5, available from Cabot, Tuscola, Ill.). Of these, PEG 3350 is the most preferred. Ideally, a semi-solid state is obtained by adding between about 8% and about 25% solidifying agent; more preferably, between about 10% and about 15% solidifier is used. The actual amount of solidifying agent needed will depend on the physical characteristics of the other exipients which are present; for example, the adjuvant MYRJ® 52 has both surfactant and thickening properties, decreasing the need for additional solidifier.

The pharmaceutical compositions of the invention may be administered by any of the methods known in the art. Such methods include but are not limited to oral administration of a suspension formed by mixing the composition of the invention with an aqueous medium such as water, milk or juice; in the form of a soft elastic or hard gelatin capsule into which the composition of the invention has been directly placed; parenteral administration including intravenous, intramuscular, intraperitoneal, intrasternal, subcutaneous and intraarticular injection or infusion; or topical administration, such as by ointments, drops or transdermal patches. Topical formulations, intended for administration to the skin or mucosa including the surfaces of the lung and eye, may be prepared directly from the compositions of the invention or from a suspension or microsuspension prepared by combining an appropriate composition of the invention with an aqueous diluent. Such topical formulations may include additional excipients as necessary, for example to modify consistency or the rate of absorption of the active ingredient.

In preparing the compositions of the present invention, the above components may be combined in any order with mixing or light agitation to ensure complete solubilization.

The pharmaceutical compositions and formulations of the invention may be administered in a sufficient amount, and for a sufficient time, as required to provide the desired therapeutic effect. The specific therapeutically effective dosage level will be dependent on a number of factors including the specific condition being treated, the severity of the disorder, the activity of the particular active ingredient, the specific formulation employed, the time and method of administration, the duration of treatment, and other factors which are well known in the medical arts.

The invention will be better understood by reference to the following examples, which are understood to be illustrative only and are not intended as a limitation upon the scope of the invention.

Preparation of Compositions

Compositions representative of the present invention were prepared by combining the active ingredient (here, cyclosporin A) with the named excipients in the proportions shown. In each case, hydrophilic phase components were first combined and mixed until uniform. Surfactant phase components were added next with mixing, which was continued until the mixture was uniform. With continued mixing, the cyclosporin was added and mixed until complete dissolution occurred. Additional hydrophilic solvents, surfactants and other adjuvants, if present, were then added with mixing to achieve the final desired proportions. In the case of the semi-solid compositions employing PEG as a thickener/solidifier (exemplified in Examples 16–24), the PEG was warmed to approximately 45° C. before being added to and mixed with the cyclosporin-containing mixture.

Using the above procedure, the compositions of Examples 1–24 were prepared.

| Component | |
|---|---|
| Example 1 | % w/v |
| Cyclosporin A | 10 |
| CREMOPHOR ® EL | 40 |
| Propylene glycol | qs 100 ml |
| Example 2 | % w/v |
| Cyclosporin A | 10 |
| CREMOPHOR ® RH40 | 40 |
| Propylene glycol | qs 100 ml |

| Component | |
|---|---|
| Example 3 | % w/v |
| Cyclosporin A | 10 |
| CREMOPHOR ® RH40 | 25 |
| Propylene glycol | qs 100 ml |
| Example 4 | % w/v |
| Cyclosporin A | 10 |
| CREMOPHOR ® EL | 10 |
| Distilled H$_2$O | 5 |
| Propylene glycol | qs 100 ml |
| Example 5 | % w/v |
| Cyclosporin A | 10 |
| Anhydrous ethanol | 20 |
| CREMOPHOR ® EL | 40 |
| PEG 400 | qs 100 ml |
| Example 6 | % w/v |
| Cyclosporin A | 10 |
| Benzyl alcohol | 2.5 |
| CREMOPHOR ® EL | 15 |
| TWEEN ® 80 | 10 |
| Propylene glycol | qs 100 ml |
| Example 7 | % w/v |
| Cyclosporin A | 10 |
| CREMOPHOR ® EL | 40 |
| Propylene glycol | qs 100 ml |
| Example 8 | % w/v |
| Cyclosporin A | 10 |
| Anhydrous ethanol | 10 |
| TWEEN ® 80 | 25 |
| Propylene glycol | qs 100 ml |
| Example 9 | % w/v |
| Cyclosporin A | 10 |
| Anhydrous ethanol | 5 |
| Propylene glycol | 5 |
| TWEEN ® 80 | 25 |
| PEG 400 | qs 100 ml |
| Example 10 | % w/v |
| Cyclosporin A | 10 |
| CREMOPHOR ® EL | 15 |
| Distilled water | 5 |
| Propylene glycol | qs 100 ml |
| Example 11 | % w/w |
| Cyclosporin A | 10 |
| Propylene glycol | 40 |
| CREMOPHOR ® EL | 50 |
| Example 12 | % w/w |
| Cyclosporin A | 10 |
| Anhydrous ethanol | 10 |
| Propylene glycol | 40 |
| CREMOPHOR ® RH40 | 40 |
| Example 13 | % w/w |
| Cyclosporin A | 10 |
| Anhydrous ethanol | 10 |
| Propylene glycol | 10 |
| PEG 400 | 25 |
| CREMOPHOR ® RH40 | 45 |
| Example 14 | % w/w |
| Cyclosporin A | 10 |
| Benzyl alcohol | 3 |
| Propylene glycol | 10 |
| PEG 400 | 32 |
| CREMOPHOR ® EL | 45 |
| Example 15 | % w/w |
| Cyclosporin A | 10 |
| Anhydrous ethanol | 8 |
| Propylene glycol | 7 |
| PEG 300 | 35 |
| CREMOPHOR ® EL | 40 |
| Example 16 | % w/w |
| Cyclosporin A | 13 |
| Anhydrous ethanol | 10 |
| Propylene glycol | 8 |
| CREMOPHOR ® RH40 | 50 |
| PEG 1450 | 19 |
| Example 17 | % w/w |
| Cyclosporin A | 13 |
| Anhydrous ethanol | 10 |
| Propylene glycol | 10 |
| CREMOPHOR ® EL | 50 |
| TWEEN ® 80 | 14 |
| CAB O SIL ® M-5 | 3 |
| Example 18 | % w/w |
| Cyclosporin A | 13 |
| Anhydrous ethanol | 9 |
| Propylene glycol | 8 |
| CREMOPHOR ® RH40 | 49 |
| PEG 3350 | 21 |
| Example 19 | % w/w |
| Cyclosporin A | 13 |
| Anhydrous ethanol | 10 |
| Propylene glycol | 10 |
| CREMOPHOR ® EL | 50 |
| PEG 1450 | 10 |
| Stearyl alcohol | 7 |
| Example 20 | % w/w |
| Cyclosporin A | 13 |
| Anhydrous ethanol | 10 |
| Propylene glycol | 10 |
| CREMOPHOR ® RH40 | 50 |
| PEG 2000 | 10 |
| TWEEN ® 80 | 5 |
| CAB O SIL ® M-5 | 2 |
| Example 21 | % w/w |
| Cyclosporin A | 13 |
| Anhydrous ethanol | 10 |
| Propylene glycol | 10 |
| CREMOPHOR ® EL | 45 |
| TWEEN ® 80 | 5 |
| PEG 1450 | 10 |
| Stearyl alcohol | 7 |
| Example 22 | % w/w |
| Cyclosporin A | 13 |
| Anhydrous ethanol | 10 |
| Propylene glycol | 10 |
| CREMOPHOR ® EL | 45 |
| MYRJ ® 52 | 12 |
| PEG 3350 | 10 |
| Example 23 | % w/w |
| Cyclosporin A | 13 |
| Anhydrous ethanol | 10 |
| Propylene glycol | 10 |
| CREMOPHOR ® EL | 45 |
| SPAN ® 80 | 12 |
| PEG 3350 | 10 |
| Example 24 | % w/w |
| Cyclosporin A | 13 |
| Anhydrous ethanol | 10 |
| Propylene glycol | 10 |
| CREMOPHOR ® EL | 37 |
| SPAN ® 80 | 20 |
| PEG 3350 | 10 |

Example 25

The oral bioavailability of the compositions of the present invention was evaluated in fasted beagle dogs as follows:

The compositions of Examples 1–24 and control samples consisting of the commercial cyclosporine products SANDIMMUNE® Oral Liquid (100 mg/ml) and OPTORAL® Oral Liquid (100 mg/ml) were administered to the subjects in amounts that delivered 50 mg cyclosporin A to each dog. (The compositions of Examples 16–24 were administered in hard gelatin capsules.) Blood concentration data were normalized to a 5 mg/kg dose in each dog.

In a typical experiment, six dogs were fasted and then, at time t=0, were given one of the compositions. Blood samples were taken at 15, 30, 60 and 90 minutes and at 2, 4, 6, 9, 12, 15 and 24 hours after dosing and analyzed for the blood concentration of cyclosporine. From these data the maximum blood serum concentration ($C_{max}$), time from dosing until maximum blood serum concentration ($T_{max}$), and total amount absorbed (AUC), as well as the respective standard deviations, were computed and are shown below in Table 1, below.

TABLE 1

Blood Concentrations of Cyclosporin A Following 5 mg/kg Oral Dosing of Dogs

| Example Number | $C_{max}$ (ng/ml) | $T_{max}$ (hours) | AUC (ng · hour/ml) |
|---|---|---|---|
| 1 | 1010.0 ± 185.3 | 1.0 ± 0.0 | 5916.5 ± 1458.0 |
| 2 | 1034.4 ± 157.0 | 1.2 ± 0.3 | 6123.3 ± 1263.1 |
| 3 | 982.8 ± 422.7 | 1.0 ± 0.0 | 6017.6 ± 1312.3 |
| 4 | 913.6 ± 85.3 | 1.3 ± 0.3 | 5035.3 ± 1016.7 |
| 5 | 1099.9 ± 449.9 | 1.1 ± 0.2 | 5198.2 ± 1772.3 |
| 6 | 1033.2 ± 382.0 | 1.1 ± 0.4 | 5274.0 ± 3394.5 |
| 7 | 783.9 ± 179.3 | 1.4 ± 0.5 | 4450.0 ± 1838.3 |
| 8 | 773.0 ± 233.0 | 1.3 ± 0.6 | 4772.9 ± 1863.7 |
| 9 | 594.9 ± 177.2 | 2.0 ± 1.0 | 4112.6 ± 2299.9 |
| 10 | 749.4 ± 244.0 | 1.2 ± 0.4 | 3796.4 ± 1220.2 |
| 11 | 1011.0 ± 153.5 | 1.3 ± 0.4 | 5271.8 ± 1184.3 |
| 12 | 1099.8 ± 170.5 | 1.1 ± 0.2 | 6126.0 ± 1229.8 |
| 13 | 1119.2 ± 226.3 | 1.7 ± 0.3 | 7243.6 ± 1965.3 |
| 14 | 1050.6 ± 349.6 | — | 5846.9 ± 1904.4 |
| 15 | 1133.5 ± 217.7 | — | 6050.7 ± 788.8 |
| 16 | 1140.5 ± 313.1 | — | 6058.0 ± 895.7 |
| 17 | 1066.3 ± 260.5 | — | 5747.3 ± 557.8 |
| 18 | 1049.9 ± 264.2 | — | 5328.7 ± 1734.2 |
| 19 | 1056.5 ± 439.0 | — | 6587.5 ± 2397.0 |
| 20 | 970.9 ± 234.7 | — | 6209.7 ± 1632.7 |
| 21 | 1191.2 ± 676.3 | — | 6952.3 ± 2199.8 |
| 22 | 1105.9 ± 354.2 | — | 6802.6 ± 1929.3 |
| 23 | 1249.8 ± 350.9 | — | 7018.0 ± 2262.7 |

For SANDIMMUNE® Oral Liquid, the $C_{max}$ was 849.2±156.1 ng/ml and the AUC was 4517.0±1318.7 ng·hour/ml. For OPTORAL® Oral Liquid the $C_{max}$ was 1045.6±138.0 ng/ml and the AUC was 5371.3±461.1 ng·hour/ml. No statistically significant were found in $C_{max}$ or AUC values between the formulations of Examples 1–23 and the above two commercially available cyclosporin formulations.

Example 26

Additional bioavailability studies were conducted in human subjects comparing certain of the semi-solid compositions of the present invention to the commercially available cyclosporine product NEORAL® (300 mg SEC). The test compositions were administered in hard gelatin capsules, and data collected as above at regular intervals. The results are shown below in Table 2, in which bioavailability is calculated as the ratio of log-transformed $C_{max}$ and AUC data for the test composition relative to comparable data for NEORAL®. ("CI" indicates the statistical confidence interval for the respective bioavailabilities.)

TABLE 2

Relative Bioavailability of Cyclosporin A

| Example No. | Relative In ($C_{max}$) | 90% CI | Relative In (AUC) | 90% CI |
|---|---|---|---|---|
| 17 | 0.758 | 0.688–0.835 | 0.729 | 0.698–0.761 |
| 21 | 0.773 | 0.700–0.854 | 0.810 | 0.775–0.846 |
| 23 | 0.856 | 0.800–0.917 | 0.839 | 0.793–0.888 |
| 24 | 0.884 | 0.819–0.955 | 0.898 | 0.847–0.953 |

The foregoing results demonstrate that the binary compositions of the present invention, which lack a lipophilic solvent phase, are nevertheless capable of delivering cyclosporin with bioavailabilities comparable to those of a ternary formulation.

The foregoing detailed description and examples are merely illustrative and are not to be construed as limitations upon the scope of the invention, which is defined solely by the appended claims and their equivalents. It is expected that various changes and modifications to the disclosed embodiments will be apparent to those skilled in the art and may be made without departing from the spirit and scope of the invention.

What is claimed is:

1. A binary pharmaceutical composition in liquid or semi-solid form, said composition comprising:
   (a) a cyclosporine;
   (b) a hydrophilic phase;
   (c) a high-HLB surfactant having an HLB of at least 10, said high-HLB surfactant being selected from the group consisting of polyoxyethylene castor oil derivatives and mono-fatty acid esters of polyoxyethylene sorbitans; and
   (d) another surfactant selected from the group consisting of sorbitan oleates, provided that (b) is not a $C_{1-5}$ alkyl or tetrahydrofurfuryl di- or partial ether of a mono- or poly-oxy alkanediol and (c) is not an ethylene oxide/propylene oxide block copolymer.

2. A binary composition according to claim 1 wherein the cyclosporine is cyclosporin A.

3. A binary composition according to claim 2 wherein the hydrophilic phase (b) comprises a hydrophilic component selected from the group consisting of water; ethanol; benzyl alcohol; propylene glycol; glycerol; dimethyl isosorbide; and polyethylene glycol.

4. A binary composition according to claim 2 wherein the hydrophilic phase (b) comprises propylene glycol.

5. A binary composition according to claim 2 wherein the hydrophilic phase (b) comprises a mixture of propylene glycol and ethanol.

6. A binary composition according to claim 2 wherein the hydrophilic phase (b) comprises a mixture of propylene glycol, polyethylene glycol and ethanol.

7. A binary composition according to any of claims 2–6 wherein the high-HLB surfactant (c) comprises polyoxyl 35 castor oil, polyoxyl 40 hydrogenated castor oil, or a combination thereof.

8. A binary composition according to claim 7 additionally comprising a solidifying agent selected from the group consisting of polyethylene glycols having a molecular weight of more than about 1,000; stearyl alcohol; colloidal silicon dioxide; and mixtures thereof.

9. A binary composition according to claim 2 comprising:
   (a) between 0.03% and 25% by weight cyclosporine;
   (b) between 10% and 90% by weight hydrophilic phase; and (c) between 10% and 90% by weight surfactant.

10. A binary composition according to claim 2 comprising:
   (a) between 5% to 15% by weight cyclosporine;
   (b) between 20% to 80% by weight hydrophilic phase; and
   (c) between 20% to 70% by weight surfactant.

11. A binary composition according to any of claims 9 and 10 additionally comprising between 8% and 25% by weight solidifying agent.

12. A binary pharmaceutical composition comprising:
   (a) cyclosporin A in an amount of between 10% and 15% by weight;
   (b) propylene glycol in an amount of between 5% and 15% by weight;
   (c) ethanol in an amount of between 5% and 15% by weight;
   (d) polyoxyethylene-glycerol-triricinoleate polyoxyl 35 castor oil in an amount of between 30% and 50% by weight;
   (e) sorbitan monooleate in an amount of between 10% and 25% by weight; and
   (f) polyethylene glycol 3350 in an amount of between 5% and 15% by weight.

* * * * *